(12) United States Patent
Matsumura et al.

(10) Patent No.: US 7,815,312 B2
(45) Date of Patent: Oct. 19, 2010

(54) OCULAR LIGHT STIMULUS APPARATUS

(75) Inventors: Kazunori Matsumura, Hamamatsu (JP); Tatsuya Fujii, Hamamatsu (JP); Masaharu Mizuochi, Hamamatsu (JP)

(73) Assignee: Kowa Company Ltd. (JP)

( * ) Notice: Subject to any disclaimer, the term of this patent is extended or adjusted under 35 U.S.C. 154(b) by 3 days.

(21) Appl. No.: 12/384,505

(22) Filed: Apr. 6, 2009

(65) Prior Publication Data

US 2009/0257027 A1    Oct. 15, 2009

(30) Foreign Application Priority Data

Apr. 10, 2008    (JP) .............................. 2008-102432

(51) Int. Cl.
*A61B 3/10* (2006.01)

(52) U.S. Cl. ...................... 351/216; 351/221

(58) Field of Classification Search ................ 351/205, 351/206, 210, 211, 213, 216, 221, 246
See application file for complete search history.

(56) References Cited

U.S. PATENT DOCUMENTS

| 4,135,791 | A | 1/1979 | Govignon |
| 7,270,414 | B2 * | 9/2007 | Matsumura et al. ......... 351/206 |
| 7,320,519 | B2 * | 1/2008 | Iwanaga et al. ............ 351/221 |
| 2007/0019160 | A1 | 1/2007 | Kleen et al. |

FOREIGN PATENT DOCUMENTS

| EP | 1312299 A1 | 5/2003 |
| EP | 1354551 A1 | 10/2003 |
| EP | 1889567 A2 | 2/2008 |
| EP | 1908399 A1 | 4/2008 |
| JP | 2002-219107 A | 8/2002 |
| JP | 2005-323815 | 11/2005 |

* cited by examiner

*Primary Examiner*—Huy K Mai
(74) *Attorney, Agent, or Firm*—Adams & Wilks

(57) ABSTRACT

Stimulus light is projected from a stimulus light source onto an ocular fundus of an eye under examination to locally stimulate the retina in order to perform a biological examination. During a biological examination, first background light is projected from an illumination light source via an objective lens, and second background light is projected from a light source from the periphery of the objective lens onto the ocular fundus. During alignment prior to a biological examination, the first background light is turned off and the second background light is projected onto the ocular fundus. During observation of the ocular fundus, the first background light projected onto the fundus is blocked, so that fundus observation or eye fixation is not disturbed by the background light. This enables accurate alignment to be carried out. Since the examinee's eye is irradiated with the second background light from the periphery of the objective lens in preparation for a biological examination, the examinee's eye can sufficiently adapt to the light during a biological examination, ensuring a reliable biological examination.

5 Claims, 4 Drawing Sheets

FIG. 3

| | ANTERIOR OCULAR SEGMENT ILLUMINATION LIGHT (INFRARED) | W.D. LIGHT (INFRARED) | F.D. LIGHT (INFRARED) | INTERNAL FIXATION LAMP (VISIBLE) | STIMULUS LIGHT (VISIBLE) | FUNDUS OBSERVATION LIGHT (INFRARED) | FIRST BACKGROUND LIGHT (ILLUMINATION SYSTEM) (VISIBLE) | SECOND BACKGROUND LIGHT (PERIPHERY OF THE OBJECTIVE LENS) (VISIBLE) |
|---|---|---|---|---|---|---|---|---|
| S1: ANTERIOR OCULAR SEGMENT ALIGNMENT MODE | ○ | × | × | ○ | × | × | × | × |
| S2: FUNDUS ALIGNMENT MODE | × | ○ | ○ | ○ | × | ○ | × | ○ |
| S3: STIMULUS MODE | × | ○ | × | ○ | ○ | ○ | ○ | ○ |
| S4: MEASUREMENT MODE | × | ○ (×) | × | △ | ○ | ○ | ○ | ○ |
| S5: MEASUREMENT END | RETURN TO ANTERIOR OCULAR SEGMENT ALIGNMENT MODE (DIFFERENT PATIENT OR OPPOSITE EYE), OR RETURN TO FUNDUS ALIGNMENT MODE (SAME EYE) | | | | | | | |

OCULAR LIGHT STIMULUS APPARATUS

BACKGROUND OF THE INVENTION

1. Field of the Invention

The present invention relates to an ocular light stimulus apparatus, and more particularly relates to an ocular light stimulus apparatus for irradiating an ocular fundus of an examinee's eye with fundus observation light and stimulus light through an objective lens, and locally stimulating a retina with the stimulus light to carry out a biological examination using a bioelectric signal from the retina.

2. Description of the Prior Art

In addition to fundus examinations by photographing an ocular fundus image, conventionally known opthalmological examinations primarily include an electroretinogram (ERG) examination in which the retina is irradiated with stimulus light to measure an action potential generated in the retina in order to carry out an opthalmological biological examination.

In an ERG examination, background light is required for illuminating the background irradiated with stimulus light, and the quality of the ERG examination is affected by the proper combination of intensity of the background light and intensity of the stimulus light. The Journal of Japanese Opthalmological Society, v92(9) (Sep. 10, 1988; from 5-(1423) to 11-(1429)) describes an effect in which visible light is used as the background light when an ERG examination is carried out by locally irradiating the macular spot on the ocular fundus with stimulus light (local ERG).

Japanese Examined Patent Publication No. 1987-16090 describes a configuration in which the ocular fundus of the examinee's eye is irradiated with stimulus light using a fundus camera, and electrical information obtained by light stimulus is displayed as an electroretinogram. Japanese Examined Patent Publication 1987-20809 proposes a configuration for observing the state and location stimulated by the local ERG stimulus light while observing a wide range of the ocular fundus using infrared light.

Furthermore, Japanese Examined Patent Publication No. 1992-19852 describes a configuration in which the ocular fundus of the examinee's eye is observed in a non-mydriatic state, and a beam of light for observing and photographing the examinee's eye is used as stimulus light. Japanese Unexamined Patent Publication No. 2005-323815 describes a configuration in which a light stimulus apparatus for irradiating the ocular fundus with stimulus light is mounted onto a fundus camera as a unit to carry out an ERG examination. Japanese Unexamined Patent Publication No. 2006-42952 discloses that the entire retinal region is irradiated with white light using a white light-emitting diode, and using this as background light, a spotlight from a high-brightness light-emitting diode is projected as stimulus light to perform a local ERG examination while observing the ocular fundus using infrared light.

A configuration is also known in which background light is projected onto the ocular fundus through an objective lens, a light source is provided at the periphery of the objective lens, and the background light is projected onto the ocular fundus from the light source (Journal of Japanese Opthalmological Society, v85(10) (Oct. 10, 1981; 9-(1521) to 19-(1531)).

As described in the Journal of Japanese Opthalmological Society, v85(10) (Oct. 10, 1981; 9-(1521) to 19-(1531), background light having a proper intensity is projected onto the ocular fundus prior to examination when an ERG examination is to be carried out. The background light is projected in advance so as to allow the examinee's eye to adapt to the light. However, since the background light is visible, there is a problem in that the internal fixation lamp is difficult to see when the background light is projected onto the ocular fundus during fundus observation. The examinee's eye does not stably fixate, and a biological examination is difficult to carry out with accurate alignment and reliability.

SUMMARY OF THE INVENTION

It is therefore an object of the present invention to provide an ocular light stimulus apparatus capable of performing accurate alignment and allowing the examinee's eye to adapt to the light to carry out a reliable biological examination.

In an ocular light stimulus apparatus according to the present invention, an ocular fundus of an examinee's eye is irradiated with fundus observation light and stimulus light through an objective lens, and a retina is locally stimulated with the stimulus light to perform a biological examination using a bioelectric signal from the retina. The ocular light stimulus apparatus comprises a projection optical system for projecting first background light through the objective lens onto the ocular fundus of the examinee's eye, and a projection optical system for projecting second background light from a periphery of the objective lens onto the ocular fundus of the examinee's eye. During fundus observation, the first background light is turned off and the second background light is projected from the periphery of the objective lens onto the ocular fundus of the examinee's eye.

In the present invention, background light projected onto the ocular fundus via the objective lens is turned off during alignment prior to a biological examination. Therefore, eye fixation via the objective lens or fundus observation via the objective lens is not disturbed by the background light, thus enabling accurate alignment to be carried out. However, since the examinee's eye is irradiated with background light from the periphery of the objective lens in preparation for a biological examination, the examinee's eye can sufficiently adapt to the light during the biological examination and a reliable biological examination can be carried out.

Further features of the invention, its nature and various advantages will be more apparent from the accompanying drawings and following detailed description of the invention.

BRIEF DESCRIPTION OF THE DRAWINGS

FIG. 3 is a chart showing the process flow for performing a local ERG examination;

DESCRIPTION OF THE PREFERRED EMBODIMENTS

Figure 1:
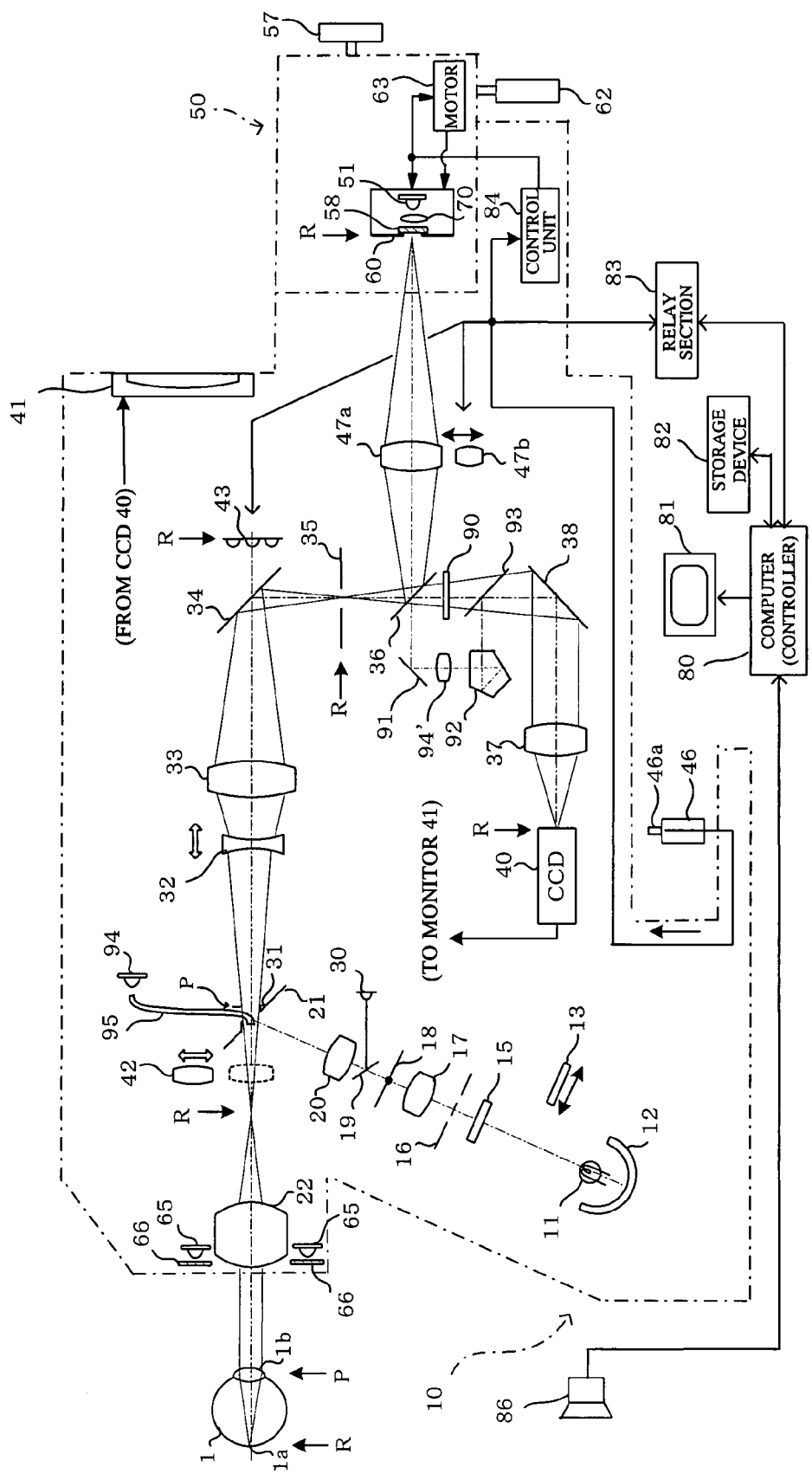
FIG. 1 is a system diagram schematically showing the overall configuration of an ocular light stimulus apparatus according to the present invention.

The present invention is described in detail below with reference to embodiments shown in the drawings.

FIG. 1 shows an opthalmological examination apparatus composed of an ocular light stimulus apparatus having a light stimulus unit 10 and a stimulus light source unit 50. In FIG. 1, the reference symbol R indicates the position conjugate with the ocular fundus 1a of the examinee's eye 1, and the reference symbol P indicates the position conjugate with the anterior ocular segment 1b (the pupil, in particular).

The light stimulus unit 10 is provided with an illumination optical system for illuminating the examinee's fundus and an imaging optical system for imaging the illuminated fundus. In the illumination optical system, a halogen lamp or another illumination light source 11 emits visible light as well as infrared light, and a portion of the light is reflected by a concave mirror 12. The visible light and infrared light from the illumination light source 11 and the visible light and infrared light reflected by the concave mirror 12 are incident on a diffusion plate 15 and diffused. The light diffused is directed to illuminate a ring slit 16 disposed in position P, which is conjugate with the anterior ocular segment (pupil) 1b of the examinee's eye 1. The illumination light from the ring slit 16 passes through a lens 17, a black spot plate 18 for removing reflection from an objective lens 22, a half mirror 19, and a relay lens 20. The illumination light is then reflected by an apertured total reflection mirror 21 having an aperture in the center, and passes through the objective lens 22 onto the ocular fundus 1a via the anterior ocular segment 1b of the examinee's eye 1, thus illuminating the ocular fundus 1a with the visible light and infrared light.

The visible light from the illumination light source 11 that is projected onto the ocular fundus is used as background light during an ERG examination, as described below. Therefore, the illumination light source 11 functions as a background light source, and the illumination optical system functions as projection optical system for projecting the background light onto the ocular fundus via the objective lens.

The visible-blocking/infrared-transmitting filter 13 is removably disposed in the illumination optical system, and when the visible-blocking/infrared-transmitting filter 13 is inserted into the optical path, the visible light from the illumination light source 11, i.e., the background light, is blocked and the ocular fundus 1a is illuminated with infrared light.

The reflected light from the ocular fundus 1a is received via the objective lens 22 and passes through the aperture of the apertured total reflection mirror 21, a photographic stop 31 disposed in the position P conjugate with the anterior ocular segment, a focus lens 32, and an imaging lens 33. The light passing through the imaging lens 33 is reflected by a half mirror 34 and incident on a half mirror 36 via a field stop 35 that is disposed in the fundus-conjugate position R. The infrared light transmitted through the half mirror 36 is reflected by a mirror 38, passes through an imaging lens 37, and is incident on an image-capturing device 40 that is disposed in the fundus-conjugate position R and composed of an infrared CCD or the like having sensitivity in the infrared and visible light regions. The signal from the image-capturing device 40 is inputted to a monitor 41.

The stimulus light source unit 50 housing a stimulus light source 51 composed of a light-emitting diode or the like for emitting visible light is mounted on the light stimulus unit 10. The stimulus light source 51 can be moved using a lever 57 within the xy plane perpendicular to the optical axis.

The stimulus light source unit 50 is provided with an indicator disc 60 in which a plurality of apertures having mutually differing diameters is formed and which is rotatably disposed in the fundus-conjugate position to make the spot diameter of the stimulus light variable. The indicator disc 60 is constructed so as to rotate by a lever 62 or a motor 63 to a position in which one of the apertures faces the stimulus light source 51 and a diffusion plate 58.

When a switch 46a provided to a joystick 46 is operated, a control unit 84 turns on the stimulus light source 51. The light from the stimulus light source 51 is guided to the diffusion plate 58 via a lens 70 and diffused by the diffusion plate 58. The diffused light is formed into stimulus light having a predetermined spot size by the selected aperture of the indicator disc 60. The stimulus light is transmitted through a variable power lens 47a (47b) and divided and reflected by the half mirror 36. The visible light reflected by the half mirror 36 is projected as stimulus light through the pupil 1b of the examinee's eye onto the ocular fundus 1a via the projection optical system composed of the half mirror 34, lenses 33, 32, the aperture of the apertured total reflection mirror 21, the objective lens 22 and the like.

Figure 2:
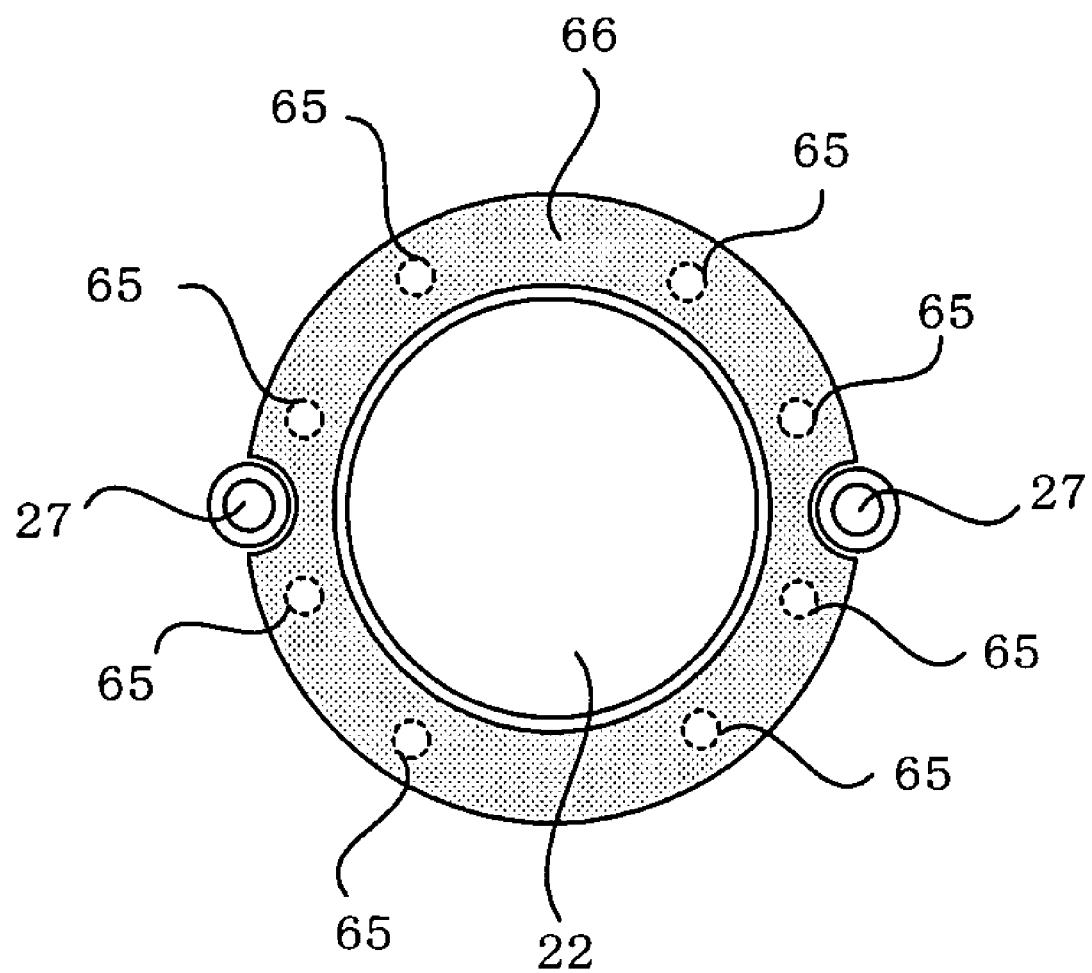
FIG. 2 is a plan view of the periphery of the objective lens of FIG. 1 as viewed from the perspective of the examinee's eye.

In an ERG examination, visible background light as well as visible stimulus light is projected onto the ocular fundus. As mentioned above, the visible light from the illumination light source 11 projected onto the ocular fundus via the objective lens 22 is used as the background light (first background light). Furthermore, a plurality of background light sources 65 for emitting visible light is disposed about the periphery of the objective lens 22, as shown in FIG. 2. The visible light from the light sources 65 is projected onto the ocular fundus via a projection optical system composed of a diffusion plate 66 or the like (a projection lens or the like is provided as needed) and is used as background light (second background light) during an ERG examination.

An ERG electrode 86 is mounted on the examinee's eye 1, and signals from the electrode are inputted to a controller (personal computer) 80 provided with a display apparatus 81 and a storage device 82. The computer 80 produces an electroretinogram, which is displayed on the display apparatus 81 and stored in the storage device 82.

The visible light from the stimulus light source 51 divided and transmitted by the half mirror 36 is reflected by the mirror 38 via a mirror 91, a lens 94', a prism 92, and an infrared-transmitting/visible light-reflecting mirror 93, and impinges on the image-capturing device 40 so that the projected indicator (stimulus light) produced by the stimulus light source 51 can be observed and displayed on the monitor 41.

A filter 90 for transmitting infrared light and reflecting visible light is inserted between the half mirror 36 and the infrared-transmitting/visible light-reflecting mirror 93 in order to prevent the visible light from the stimulus light source 51, which is divided and reflected by the half mirror 36, from being reflected by the surface of the imaging lens 33 and returned as reflected light onto the image-capturing device 40. In this case, the filter 90 has the infrared-transmitting characteristics, so that the infrared observation light is made incident on the image-capturing device 40 without being blocked by the filter 90.

A working-distance light source 94 (hereinafter referred to as "WD light source") is provided for alignment.

The WD light source 94 is composed of an infrared light-emitting diode and produces infrared light, which is directed adjacent to the center of the aperture of the apertured total reflection mirror 21 via an optical fiber 95 to form a working distance marker. The working distance marker is projected onto the cornea of the examinee's eye 1 via the objective lens 22. In order to establish an appropriate working distance, the light specularly reflected by the cornea of the examinee's eye 1 is adjusted so as to be substantially afocal.

The illumination optical system is provided with a focus-dot light source 30 composed of an infrared light-emitting diode. The infrared light from the light source 30 is projected on the ocular fundus 1a via the half mirror 19. The position of the focus dot varies in accordance with the movement of the focus lens 32, so that an examiner observes the focus dot to bring the examinee's eye into focus.

In the initial stage of alignment, an anterior ocular segment observation lens 42 is inserted on the side of the objective lens 22 opposite to the examinee's eye, and the anterior ocular segment is illuminated with infrared light from an anterior ocular illumination light source 27 disposed in the vicinity of the objective lens 22, as shown in FIG. 2. The examiner can check the image of the anterior ocular segment 1b of the examinee's eye 1 on the monitor 41 and align the apparatus on the basis of the image of the anterior ocular segment. During the alignment and the focusing operation, an internal fixation lamp 43 for emitting visible light is turned on and the examiner can make sure of the alignment and focusing operation by having the examinee view the fixation lamp.

A computer (controller) 80 can set various measurement conditions in order to perform a local ERG examination. Examples of measurement conditions include the intensity of the background light (quantity of light) obtained from the light sources 11, 65; the intensity of the stimulus light (quantity of light) from the stimulus light source 51; the wavelength component of the background light and stimulus light; the spot diameter of the stimulus light (the aperture position of the indicator disc 60); the time (lamp-on time) during which the stimulus light is emitted; the number of times the stimulus light is emitted; the blinking cycle of the stimulus light (when blinking is used even in the alignment state); the position of the fixation lamp 43; the on/off state of the light sources 11, 65, 27, 30, 94, 51; and the insertion/removal of the visible-blocking/infrared-transmitting filter 13 into/from the optical path.

Of course, the hard-ware can be so modified that the control unit 84 inside the light stimulus unit 10 takes over the entire control carried out in the computer 80. Conversely, it is also possible to configure the system so that the computer 80 outside of the light stimulus unit 10 takes over the entire control carried out by the control unit 84 inside the light stimulus unit 10. The assignment of these roles is a matter of design that can be arbitrarily determined.

In the present embodiment, a relay section 83 is provided between the light stimulus unit and the computer 80 in order to synchronize retinal stimulus with the measurement conditions set by the computer 80. The relay section 83 may be provided inside the light stimulus unit or may be taken over by the computer 80.

In such a configuration, the process flow for carrying out alignment with the examinee's eye and performing a local ERG examination is described in accordance with the chart shown in FIG. 3. The circles in FIG. 3 indicate that the quantity of light is normal. The triangles indicate that the quantity of light is small, and the X-signs indicate that there is no quantity of light, i.e., that the light source for emitting the light is turned off and is in a perfectly blocked state, or a substantially blocked state in which light is sufficiently reduced and is essentially the same as the turned-off light source. "W.D. light" refers to working-distance light from the WD light source 94, and "F.D. light" refers to focus-dot light from the focus-dot light source 30.

First, in the anterior ocular segment alignment mode (S1), the internal fixation lamp 43 is turned on and the examinee views the fixation lamp. The anterior ocular illumination light source 27 is turned on in order to illuminate the anterior ocular segment 1b of the examinee's eye with infrared light. The examiner observes the image of the anterior ocular segment on the monitor 41 and performs anterior ocular segment alignment. Since the WD operation and the focus operation are not performed in this stage, the WD light source 94 and the focus-dot light source 30, respectively, are turned off. A background light source, i.e., the illumination light source 11, for emitting first background light, the background light source 65 for emitting second background light emitted from the periphery of the objective lens, and the stimulus light source 51 are not required for anterior ocular segment alignment, and are therefore turned off, thereby emitting no fundus observation light (infrared light from the illumination light source 11), no first and second background light, and no stimulus light.

In this state, the first and second background light is not projected onto the ocular fundus, improving the visibility of the internal fixation lamp and stabilizing the fixation of the examinee's eye.

Next, in the fundus alignment mode (S2), the anterior ocular segment observation lens 42 is removed from the optical path, and the anterior ocular illumination light source 27 is turned off beginning from this mode and throughout the following modes. The stimulus light source 51 is kept off. On the other hand, the WD light source 94, the focus-dot light source 30, and the illumination light source 11 are turned on, and the visible-blocking/infrared-transmitting filter 13 is inserted into the optical path in order to block visible light, i.e., the first background light. The ocular fundus is illuminated by the fundus observation light (infrared light) from the illumination light source 11, and the working distance and focus are adjusted while the fundus image is observed on the monitor 41. During the fundus observation, the background light source 65 is turned on in order to allow the examinee's eye to adapt to the light in preparation for the ERG examination to be subsequently performed. Thus, the second background light is projected onto the ocular fundus 1a of the examinee's eye from the periphery of the objective lens 22. In this case, the visible-blocking/infrared-transmitting filter 13 blocks the first background light, so that the quantity of light is reduced by a quantity equivalent to the quantity of first background light in comparison with the total quantity of background light during the ERG examination.

When light adaptation has a priority, the quantity of second background light may be increased so as not to worsen the visibility of the internal fixation lamp. Since the pupil diameter sometimes varies in accordance with the quantity of the second background light, the quantity of light from the illumination light source 11 can be adjusted in accordance with the pupil diameter. For example, the pupil diameter may be reduced when the quantity of second background light is high. Therefore, the quantity of light from the illumination light source 11 may be set higher in accordance with the pupil diameter using a rotary switch (not shown) or the like in order to increase the infrared light projected onto the ocular fundus.

The first background light projected onto the fundus via the objective lens 22 is blocked during fundus alignment. This ensures that the fundus observation via the objective lens 22 or the eye fixation via the objective lens 22 is not disturbed by the background light, thus allowing accurate alignment to be performed. Since the examinee's fundus is irradiated with the second background light from the periphery of the objective lens 22, the examinee's eye can be adapted sufficiently to the light.

When the fundus alignment and focus adjustment has been completed, the biological examination is started. First, in the stimulus mode (S3), the stimulus light source 51 is turned on to locally stimulate the retina of the examinee's eye. This causes a bioelectric signal to be generated from the retina. At this point, the focus-dot light source 30 is turned off because the focus-dot light disturbs the monitoring. The other light sources 11, 65, 94 and the internal fixation lamp 43 are left on. Since the visible-blocking/infrared-transmitting filter 13 is removed from the optical path, the visible light from the illumination light source 11 is projected onto the fundus as first background light. The position of the stimulus light from the stimulus light source 51 can be varied within the xy plane perpendicular to the optical axis, as described above, and the spot size of the stimulus light can be varied by the indicator disc 60. The quantity of the stimulus light and the quantity of the first background light are adjusted to a quantity set by a rotary switch or the like.

Next, the process proceeds to the measurement mode (S4), and the bioelectric signal from the ERG electrode 86 is inputted to the computer 80. The computer 80 produces an electroretinogram, which is displayed on the display apparatus 81 and stored in the storage device 82. The turned-on state and the quantity of light from the light sources in the measurement mode are essentially the same as in the stimulus mode, but the WD light source 94 is turned off when necessary, and the light emitted by the internal fixation lamp 43 is reduced in order to reduce the effect on measurements.

When the measurement of the ERG has been completed (S5), the process returns to anterior ocular segment alignment (S1), and the same process is carried out for the eye of a different examinee, the opposite eye of the same examinee, or the same eye of the same examinee.

Figure 4:
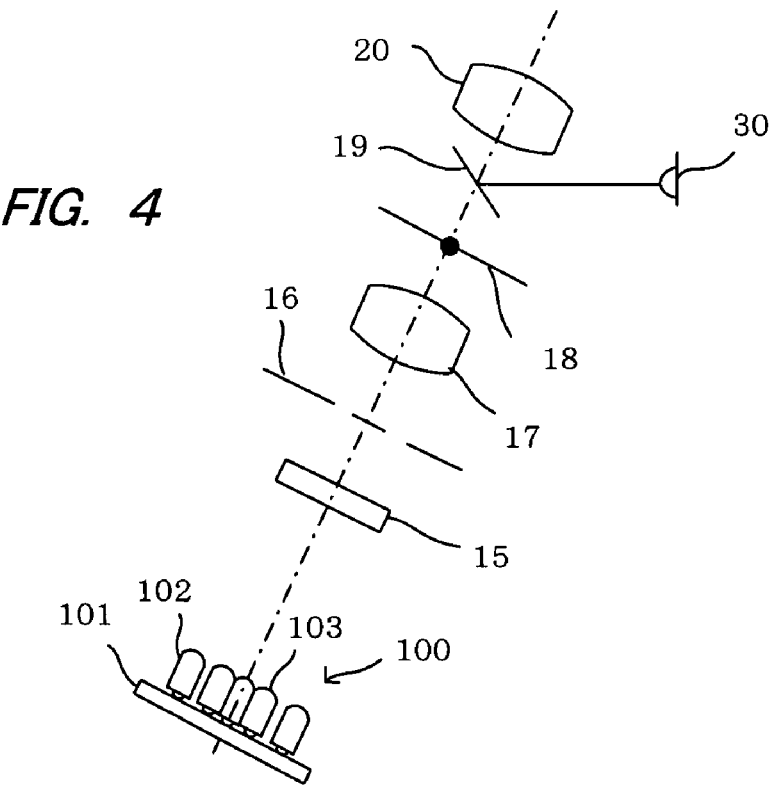
FIG. 4 is an optical diagram showing another embodiment of an illumination light source unit of the ocular light stimulus apparatus of the present invention.
Figure 5:
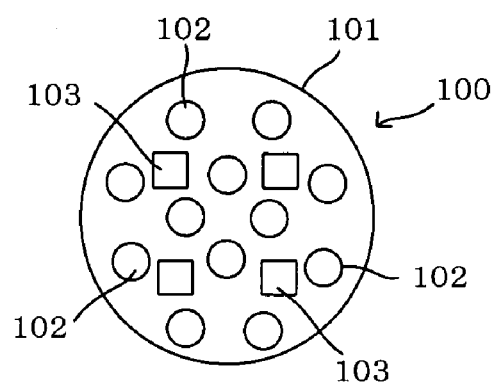
FIG. 5 is an illustrative view showing the LED arrangement of the light source unit of FIG. 4.

In the ocular light stimulus apparatus of the present invention, a light source 100 having a plurality of semiconductor light-emitting elements (LED) disposed side-by-side on a base 101 as shown in FIGS. 4 and 5 may be used in place of the light source 11 of FIG. 1. In this case, a plurality of LEDs 102 for emitting infrared light and LEDs 103 for emitting visible light is arranged in the manner as shown in FIG. 5. In such a light source 100, the visible-blocking/infrared-transmitting filter 13 can be dispensed with by selectively causing the LEDs 102, 103 to emit light.

In other words, the light source 100 can be made into an infrared light source by turning on the LEDs 102, and the light source 100 can be made into a visible light source by turning on the LEDs 103. Such a light source 100 provides an advantage in terms of noise and heat generation in comparison with the light source 11 composed of the halogen lamp of FIG. 1. Additionally, the quantity of the infrared light and the visible light can be independently adjusted. This, therefore, allows the quantity of the first background light, second background light, and illumination light for fundus observation to be adjusted arbitrarily and well balanced. Accordingly, when emphasis is placed on light adaptation as described above, the quantity of the second background light may be increased within a range in which the visibility of the fixation lamp doesn't worsen. This means that light adaptation can be achieved in a state that is more proximate to that during measurement. Also, it is sometimes the case that the pupil diameter varies and the brightness of the fundus image varies in accordance with the quantity of the background light. Accordingly, it is possible to adjust the quantity of the infrared illumination light for fundus observation in accordance with such variations.

In FIG. 5, the LEDs 103 for emitting visible light are shown as rectangles, but this option is adopted for the sake of convenience in order to differentiate from the LEDs 102 (shown as circles in the diagram) for emitting infrared light, and these shapes do not necessarily indicate the actual shapes.

What is claimed is:

1. An ocular light stimulus apparatus for irradiating an ocular fundus of an examinee's eye with fundus observation light and stimulus light through an objective lens, and locally stimulating a retina with the stimulus light to perform a biological examination using a bioelectric signal from the retina, the ocular light stimulus apparatus comprising:
   a projection optical system for projecting first background light through the objective lens onto the ocular fundus of the examinee's eye; and
   a projection optical system for projecting second background light from a periphery of the objective lens onto the ocular fundus of the examinee's eye,
   wherein, during fundus observation, the first background light is turned off and the second background light is projected from the periphery of the objective lens onto the ocular fundus of the examinee's eye.

2. An ocular light stimulus apparatus according to claim 1, wherein an anterior ocular segment observation lens is removably disposed in the vicinity of the objective lens, and the first and second background light is turned off when the anterior ocular segment observation lens is inserted in the vicinity of the objective lens.

3. An ocular light stimulus apparatus according to claim 2, wherein fundus observation light is turned off when the anterior ocular segment observation lens is inserted.

4. An ocular light stimulus apparatus according to claim 1, wherein the intensity of the fundus observation light is corrected in accordance with the intensity of the second background light.

5. An ocular light stimulus apparatus according to claim 1, wherein the fundus observation light and the first background light are projected onto the ocular fundus of the examinee's eye via a ring slit disposed in an illumination optical system.

* * * * *